United States Patent
Zukiwski et al.

(10) Patent No.: US 11,672,762 B2
(45) Date of Patent: Jun. 13, 2023

(54) ONAPRISTONE EXTENDED-RELEASE COMPOSITIONS AND METHODS

(71) Applicant: Context Biopharma Inc.

(72) Inventors: Alexander Zukiwski, Clarksburg, MD (US); Stefan Proniuk, Austin, TX (US)

(73) Assignee: CONTEXT BIOPHARMA, INC., Philadelphia, PA (US)

( * ) Notice: Subject to any disclaimer, the term of this patent is extended or adjusted under 35 U.S.C. 154(b) by 0 days.

(21) Appl. No.: 17/035,544

(22) Filed: Sep. 28, 2020

(65) Prior Publication Data
US 2021/0220279 A1  Jul. 22, 2021

Related U.S. Application Data

(63) Continuation of application No. 14/942,809, filed on Nov. 16, 2015, now Pat. No. 10,786,461.

(60) Provisional application No. 62/080,868, filed on Nov. 17, 2014.

(51) Int. Cl.
*A61K 9/20* (2006.01)
*A61K 31/575* (2006.01)

(52) U.S. Cl.
CPC .............. *A61K 9/20* (2013.01); *A61K 9/2054* (2013.01); *A61K 31/575* (2013.01)

(58) Field of Classification Search
CPC ....... A61K 9/20; A61K 9/2054; A61K 31/575
See application file for complete search history.

(56) References Cited

U.S. PATENT DOCUMENTS

| | | | |
|---|---|---|---|
| 4,742,000 A | 5/1988 | Greene | |
| 4,774,236 A | 9/1988 | Cook et al. | |
| 4,780,461 A | 10/1988 | Neef et al. | |
| 4,843,157 A | 6/1989 | Neef et al. | |
| 5,141,961 A | 8/1992 | Coapman | |
| 5,273,971 A | 12/1993 | Scholz et al. | |
| 5,283,190 A | 2/1994 | Traish et al. | |
| 5,446,036 A | 8/1995 | Scholz et al. | |
| 5,693,628 A | 12/1997 | Schubert et al. | |
| 6,093,707 A | 7/2000 | Cook et al. | |
| 6,143,754 A | 11/2000 | Chwalisz et al. | |
| 6,537,584 B1 | 3/2003 | Zentner et al. | |
| 6,750,015 B2 | 6/2004 | Horwitz et al. | |
| 6,900,193 B1 | 5/2005 | Kim et al. | |
| 7,678,781 B2 | 3/2010 | Fiordeliso et al. | |
| 8,121,365 B2 | 2/2012 | Pinard et al. | |
| 8,709,463 B2 | 4/2014 | Looney et al. | |
| 9,046,534 B2 | 6/2015 | Gilles | |
| 9,074,002 B2 | 7/2015 | Tonks et al. | |
| 9,193,757 B2 | 11/2015 | Proniuk | |
| 9,328,346 B2 | 5/2016 | Lee et al. | |
| 9,618,512 B2 | 4/2017 | Endou et al. | |
| 2003/0099641 A1 | 5/2003 | Smith et al. | |
| 2004/0072811 A1 | 4/2004 | Hoffmann et al. | |
| 2004/0121304 A1 | 6/2004 | Fuhrmann et al. | |
| 2004/0141980 A1 | 7/2004 | Ignjatovic et al. | |
| 2006/0063190 A1 | 3/2006 | Fischer et al. | |
| 2006/0111577 A1 | 5/2006 | Kim et al. | |
| 2007/0166372 A1 | 7/2007 | Huang et al. | |
| 2007/0166753 A1 | 7/2007 | Mass | |
| 2007/0167971 A1 | 7/2007 | Huey et al. | |
| 2008/0200440 A1 | 8/2008 | Fuhrmann et al. | |
| 2011/0003753 A1 | 1/2011 | Waxman et al. | |
| 2011/0053900 A1 | 3/2011 | Podolski et al. | |
| 2011/0293511 A1 | 12/2011 | Johns et al. | |
| 2012/0010790 A1 | 1/2012 | Kanayama et al. | |
| 2012/0140790 A1 | 6/2012 | Ali et al. | |
| 2012/0230983 A1 | 9/2012 | Muller et al. | |
| 2013/0018027 A1 | 1/2013 | Podolski et al. | |
| 2013/0029953 A1* | 1/2013 | Nickisch ................. | A61P 35/00 514/173 |
| 2013/0095170 A1 | 4/2013 | Gilles | |
| 2013/0316992 A1 | 11/2013 | Lange et al. | |
| 2013/0338016 A1 | 12/2013 | McDonough et al. | |
| 2014/0127219 A1 | 5/2014 | Sahin et al. | |
| 2014/0271819 A1* | 9/2014 | Proniuk ............... | A61K 31/569 424/450 |
| 2014/0363425 A1 | 12/2014 | Graham et al. | |
| 2015/0241432 A1 | 8/2015 | Berois et al. | |
| 2015/0241435 A1 | 8/2015 | Gilles | |
| 2015/0285803 A1 | 10/2015 | Gilles et al. | |
| 2016/0166583 A1 | 6/2016 | Zukiwski et al. | |
| 2017/0088579 A1 | 3/2017 | Tilstam et al. | |
| 2017/0182065 A1 | 6/2017 | Brittain et al. | |
| 2017/0266204 A1 | 9/2017 | Proniuk et al. | |

FOREIGN PATENT DOCUMENTS

| | | |
|---|---|---|
| CN | 1087090 A | 5/1994 |
| CN | 103483449 A | 1/2014 |

(Continued)

OTHER PUBLICATIONS

A0A2V9M896_9BACT, UniProtKB Accession No. A0A2V9M896_9BACT, Siaidase domain-containing protein, Sep. 12, 2018 [Online], Retrieved on May 22, 2020. Retrieved from the Internet: < URL: https://www.uniprot.org/Uniprot/A0a2v9m896 > Entire document.

Ace, C. et al., "Microarray profiling of progesterone-regulated endometrial genes during the rhesus monkey secretory phase." (2004) Reprod Biol Endocrinol 2: 54.

Ariga, N. et al: "Progesterone receptor A and B isoforms in the human breast and its disorders", (2001) Jpn J. Cancer Res. vol. 92, No. 3, 302-308.

(Continued)

*Primary Examiner* — Genevieve S Alley

(74) *Attorney, Agent, or Firm* — Goodwin Procter LLP

(57) ABSTRACT

Onapristone extended-release formulations and methods of administering onapristone extended-release formulations are provided. Onapristone extended-release formulations provide sufficient therapeutic activity as compared to immediate-release formulations with reduced potential for adverse side effects.

21 Claims, 4 Drawing Sheets

(56) References Cited

FOREIGN PATENT DOCUMENTS

| | | |
|---|---|---|
| DE | 3321826 A1 | 12/1984 |
| EP | 0129499 A2 | 12/1984 |
| EP | 0277676 A1 | 8/1988 |
| EP | 0447014 A2 | 9/1991 |
| EP | 0803250 A1 | 10/1997 |
| EP | 2075246 A1 | 7/2009 |
| JP | H07509218 A | 10/1995 |
| JP | 2011511011 A | 4/2011 |
| JP | 2012533539 A | 12/2012 |
| WO | 1998031702 A1 | 7/1998 |
| WO | 2002072813 A1 | 9/2002 |
| WO | 2006010097 A2 | 1/2006 |
| WO | 2006111856 A1 | 10/2006 |
| WO | 2007078599 A2 | 7/2007 |
| WO | 2008128783 A2 | 10/2008 |
| WO | 2009025759 A1 | 2/2009 |
| WO | 2009134725 A2 | 11/2009 |
| WO | 2012083017 A2 | 6/2012 |
| WO | 2012087983 A1 | 6/2012 |
| WO | 2012122514 A1 | 9/2012 |
| WO | 2013016725 A1 | 1/2013 |
| WO | 2013052652 A1 | 4/2013 |
| WO | 2013086379 A3 | 8/2013 |
| WO | 2014093918 A1 | 6/2014 |
| WO | 2014164861 A1 | 10/2014 |
| WO | 2014197653 A2 | 12/2014 |
| WO | 2016154203 A1 | 9/2016 |
| WO | 2017192567 A1 | 11/2017 |
| WO | 2018067198 A1 | 4/2018 |

OTHER PUBLICATIONS

Arnett-Mansfield, et al., "Focal Subnuclear Distribution of Progesterone Receptor is Ligand Dependent and Associated with Transcriptional Activity," Mol Endocrinol, Jan. 2007, vol. 2, No. 1, pp. 14-29.
Arnett-Mansfield, et al., "Subnuclear Distribution of Progesterone Receptors A and B in Normal and Malignant Endometrium", J Clin Endocrinol Metab, (2004) vol. 89, No. 3, pp. 1429-1442.
Bailey, T. et al., "MEME: discovering and analyzing DNA and protein sequence motifs." (2006) Nucleic Acids Res 34: W369-373.
Bailey, T., et al., "The value of position-specific priors in motif discovery using MEME." (2010) BMC Bioinformatics 11: 179.
Baillie et al., "Role of Biotransformation in Drug-Induced Toxicity: Influence of Intra-and Inter-Species Differences in Drug Metabolism", (2011) 26(1): 15-29.
Ballare, C. et al., "Nucleosome-Driven Transcription Factor Binding and Gene Regulation." (2013) Molecular Cell 49, 1-13.
Bamberger et al. "Progesterone receptor isoforms, PR-Band PR-A, in breast cancer: Correlations with clinicopathologic tumor parameters and expression of AP-1 factors", Horm Res (2000) CH. vol 54: 32-37.
Beck, C. A. et al., "Two Types of Anti-progestins Have Distinct Effects on Site-specific Phosphorylation of Human Progesterone Receptor", The Journal of Biological Chemistry (1996) 271: 1209-1217.
Beguelin, W. et al., "Progesterone receptor induces ErbB-2 nuclear translocation to promote breast cancer growlh via a novel transcriptional effect: ErbB-2 function as a coactivator of Stat3." (2010) Mol Cell Biol 30: 5456-5472.
Belikov, S. et al., "FoxA 1 binding directs chromatin structure and the functional response of a glucocorticoid receptor-regulated promoter" (2009) Mol Cell Biol 29: 5413-5425.
Benagiano, G. et al., "Selective progesterone receptor modulators 3: use in oncology, endocrinology and psychiatry", Expert Opin. Pharmacother (2008) 9:2487-2496.
Beral, V. et al., "Breast cancer and hormone-replacement therapy in the Million Women Study." (2003) Lancet 362: 119-427.
Beral, V. et al., "Breast Cancer Risk in Relation to the Interval Between Menopause and Starting Hormone Therapy." (2011) J Natl Cancer Inst 103: 296-305.

Bergström et al. "Accuracy of calculated pH-dependent aqueous drug solubility", European J. Pharmaceutical Sciences, (2004) vol. 22, pp. 387-398.
Bernardo, G. et al., FOXA1 is an essential determinant of ERalpha expression and mammary ductal morphogenesis. (2010) Development 137: 2045-2054.
Blankenstein, M. et al., "Occurrence, regulation, and significance of progesterone receptors in human meningiome", Steroids (2000) 65: 795-800.
Bolton, C. et al. "Cell- and gene-specific regulation of primary target genes by the androgen receptor. ", (2007) Genes Dev 21: 2005-2017.
Bonkhoff, H et al., "Progesterone Receptor Expression in Human Prostate Cancer: Correlation With Tumor Progression. Prostate" (2001) 48: 285-291.
Bonneterre et al., "Abstract P5-02-13: Triple negative breast cancer the impact of isotype-specific progesterone receptor antibodies on the diagnosis results Cancer Researeh", (2015) vol. 75; 9, pp. P5-02-13, 1538-7445.
Bonneterre, J. et al., "Development of a technique to detect the activated form of the progesterone receptor and correlation with clinical and histopathological characteristics of endometrioid adenocarcinoma of the uterine corpus", Gynecologic Oncology (2015) doi: 10.1016/j.ygyno.2015.06.037.
Borthwick, J. et al., "Determination of the transcript profile of human endometrium ", (2003) Mol Hum Reprod 9: 19-33.
Bravieri, R. et al., "Different DNA contact schemes are used by two winged helix proteins to recognize a DNA binding sequence." (1997) Nucleic Acids Res 25: 2888-2896.
Cameron, S. et al., "Critchley HOD, Buckley CH et al. The effects of post-ovulatory administration of onapristone on the development of a secretory endometrium", Human Reproduction (1996) 11 (1):40-49.
Cameron, S. et al., "Effects of onapristone on postmenopausal endometrium. Steroids", (2003) 68: 1053-1059.
Cantillo (Kappe) et al. "A Continuous-Flow Protocol for Light-Induced Benzylic Fluorinations" J. Org. Chem., 2014, 79 (17), pp. 8486-8490.
Carroll, J. et al., "Genome-wide analysis of estrogen receptor binding sites." (2006) Nat Genet 38: 1289-1297.
Chan, S. Y., "The development of PVP-based solid dispersions using hot melt extrusion for the prepaation of immediate release formulations," Thesis for PhD, (2013) School of Pharmacy University of East Anglia.
Chapman et al., "GenePattern 2.0; Nature Genetics" Nature Publishing Group (2006); vol. 38, No_5.
Chen et al., "A facile nanoaggregation strategy for oral delivery of hydrophobic drugs by utilizing acid-base neutralization reactions", (2008) Nanotechnology 19: 375104, pp. 1-7.
Chlebowski, R et al., "Estrogen plus progestin and breast cancer incidence and mortality in postmenopausal women." (2010) JAMA 304: 1684-1692.
Cicatiello, L. et al., "Estrogens and progesterone promote persistent CCND1 gene activation during G1 by inducing transcriptional derepression via c-Jun/c-Fos/estrogen receptor (progesterone receptor) complex assembly to a distal regulatory element and recruitment of cyclin D1 to its own gene promoter." (2004) Mol Cell Biol 24: 7260-7274.
Cirillo LA, Zaret KS (2007) Specific interactions of the wing domains of FOXA 1 transcription factor with DNA. J Mol Biol 366: 720-724.
Clarke, C. et al., "Monoclonal antibodies to human progesterone receptor: characterization by biochemical and immunohistochemical techniques." (1987) Endocrinology 121: 1123-1132.
Clarke, C. et al., "Non-Overiapping Progesterone Receptor Cistromes Contribute to Cell-Specific Transcriptional Outcomes." (2012) PLoS ONE 7(4): e35859. doi:10.1371/journal.pone.0035859.
Clarke, C. et al., "Progestin regulation of cellular proliferation." (1990) Endocr Rev 11: 266-301.
Cottu, P. et al., "Onapristone (ONA) in progesterone receptor (PR)-expressing tumors: Efficacy and biomarker results of a dose-escalation phase 1 study", J. Clin. Oncol. (2015) 33 (suppl; abstr 5593).

(56) References Cited

OTHER PUBLICATIONS

Croxatto, H. et al., "Effect of the antiprogestin onapristone on follicular growth in women", Human Reproduction (1994) 9: 1442-1447.

EP15776251.9 partial supplementary European search report (R 164 EPC) dated Nov. 7, 2017.

Etreby, et al., "Antitumor Activity of Mifepristone in the Human LNCaP, LNCaP-C4, and LNCaP-C4-2 Prostate Dancer Models in Nude Mice", The Prostate, 2000, vol. 42, No. 2, pp. 99-106.

Examination Report of Australian Patent Application 2012318618, dated Aug. 9, 2016.

Examination Report of New Zealand Patent Application No. 623140 dated Dec. 8, 2014.

Extended European Search Report of European Patent Application No. 12837954.2 dated Apr. 17, 2015.

Faivre, E. et al., "Progesterone receptor rapid signaling mediates serine 345 phosphorylation and tethering to specificity protein 1 transcription factors." (2008) Mol Endocrinol 22: 823-837.

Ferland "Synthetic Cardenolides and Related Products. III. Isocardenolides," Canadian Journal of Chemistry (1974) 52,, pp. 1642-1661.

Final Office Action dated Aug. 27, 2019 U.S. Appl. No. 15/825,697.
Final Office Action dated Feb. 20, 2020 U.S. Appl. No. 14/942,809.
Final Office Action dated May 11, 2018 in U.S. Appl. No. 15/378,004.

Lange, C. et al., "Progesterone Receptor Action: Translating Studies in Breast Cancer Models to Clinical Insights", Innov Endocrinol Cancer (2008) 7: 94-110.

Langmead, B. et al., "Ultrafast and memory-efficient alignment of short DNA sequences to the human genome." (2009) Genome Biol 10: R25.

Lasonos, A. et al., "Scientific Review of Phase I Protocols With Novel Dose-Escalation Designs: How Much Information is Needed? ", Journal of Clinical Oncology (2015) JCO. 2014.59. 8466.

Lieberman, B. et al., "The constitution of a progesterone response element." (1993) Mol Endocrinol 7: 515-527.

Liu, Z. et al., "Sequential recruitment of steroid receptor coactivator-1 (SRC-1) 5 and p300 enhances progesterone receptor-dependent initiation and reinitiation of transcription from chromatin." (2001) Proc Natl Acad Sci U S A 98: 12426-12431.

Longacre, T. "A correlative morphologic study of human breast and endometrium in the menstrual cycle." (1986) Am J Surg Pathol 10: 382-393.

Lupien, M. et al., "FoxA 1 translates epigenetic signatures into enhancer-driven lineage-specific transcription." (2008) Cell 132: 958-970.

MacQuarrie, K. et al., "Genome-wide transcription factor binding: beyond direct target regulation." (2011) Trends Genetics 27: 141-148.

McGowan et al., "Cytoskeletal Responsiveness to Progestins is Dependent on Progesterone Receptor A Levels," Journal of Molecular Endocrinology, 2003, 31, pp. 241-253.

McKenna, N. et al., "Combinatorial control of gene expression by nuclear receptors and coregulators." (2002) Cell 108: 465-474.

Metzger, E. et al., "LSD1 demethylates repressive histone marks to promote androgen-receptor-dependent transcription.", Nature (2005) 437: 436-439.

Meuleman et al., "Morphological and Biochemical Characterization of a Human Liver in a uPA-SCID Mouse Chimera", Hepatology (2005) 41 (4); 847-856.

Mortazavi, A. et al., "Mapping and quantifying mammalian transcriptomes by RNA-Seq.", (2008) Nat Methods 5: 621-628.

Mortel, R. et al., "Heterogeneity and Progesterone-Receptor Distribution in Endometrial Adenocarcinoma", Cancer (1984)53:113-116.

Mote et al. "Detection of progesterone receptor forms A and B by immunohistochemical analysis", (2001) J. Clin. Pathol. 54: 624-630.

Mote, P. "Relative expression of progesterone receptors A and B in premalignant and invasive breast lesions", Breast Dancer Research (2000) 2 (Suppl 1) P2.01 doi:1 0.1186/bcrl 03.

Mote, P. et al., "Loss of co-ordinate expression of progesterone receptors A and B is an early event in breast carcinogenesis". Breast Cancer Res Treat (2002) 72(2): 163-72.

Mote, P. et al., "Progesterone receptor isoforms in normal and malignant breast", Ernst Schering Found Symp Proc. (2007) (1):77-107.

Mou et al., "Potent dried drug nanosuspensions for oral bioavailability enhancement of poorly soluble drugs with pH-dependent solubility", (2011) International Journal of Pharmaceutics 413, pp. 237-244.

Murtagh, J. et al., "The Nuclear Factor I (NFI) gene family in mammary gland development and function.", (2003) J Mammary Gland Biol Neoplasia 8: 241-254.

Nadji, M. "Immunohistochemistry of Estorgen and Progesterone Receptors Reconsidered: Experience With 5,993 Breast Cancers", Anatomic Pathol. (2005) 123: 21-27.

Neef et al., "New Steroids by Simmons-Smith Methyenation and Subsequent Rearrangement", J_ Org_ Chem., (1987) vol. 52, No_ 18 pp. 4143-4146.

Neef, G. et al., "New steroids with antiprogestational and antiglucocorticoid activities", (1984) 44, 349-372.

Nelson, C. et al., "Determinants of DNA sequence specificity of the androgen, progesterone, and glucocorticoid receptors: evidence for differential steroid receptor response elements." (1999) Mol Endocrinol 13: 2090-2107.

Non-Final Office Action issued in U.S. Appl. No. 14/942,809, dated Jan. 6, 2017.
Non-Final Office Action dated Apr. 8, 2021 U.S. Appl. No. 16/720,425.
Non-Final Office Action dated Feb. 19, 2019 inU.S. Appl. No. 15/464,085.
Non-Final Office Action dated Feb. 8, 2019 in U.S. Appl. No. 15/378,004.
Non-Final Office Action dated Jan. 23, 2019 in U.S. Appl. No. 14/681,032.
Non-Final Office Action dated Mar. 6, 2015 in U.S. Appl. No. 14/205,694.
Non-Final Office Action dated May 13, 2019 in U.S. Appl. No. 14/698,100.
Non-Final Office Action dated May 15, 2019 in U.S. Appl. No. 14/942,809.
Non-Final Office Action dated Nov. 27, 2018 in U.S. Appl. No. 15/825,697.
Notice of Allowance received in U.S. Appl. No. 14/942,809 dated May 27, 2020.
Notice of Allowance received in U.S. Appl. No. 15/274,555 dated Jan. 15, 2019.
Notice of Allowance received in U.S. Appl. No. 15/378,004 dated Sep. 25, 2019.
Notice of Allowance received in U.S. Appl. No. 15/825,697 dated Aug. 9, 2018.

Onate, S. et al., "Sequence and characterization of a coactivator for the steroid hormone receptor superfamily." (1995) Science 270: 1354-1357.

Pearson, P. Wienkers, editors. Handbook of drug metabolism:, New York: Informa Healthcare; 2009. pp. 445-464.

Pierrou, S. et al., "Cloning and characterization of seven human forkhead proteins: binding site specificity and DNA pending." (1994) EMBO J 13: 5002-5012.

Press, M. et al. "Comparison of different antibodies for detection of progesterone receptor in breast cancer", Steroids (2002) 67:799-813.

Puma, et al., Dimensionless analysis of slurry photocatalytic reactors using two-flux and six-flux radiation absorptionscattering models, Catalysis Today, 2007, 122, pp. 78-90.

Puma, G. L., "Photocatalytic oxidation of multicomponent systems of herbicides: scale-up of laboratory kinetics rate data to plant scale" Catal. Today 2007, 124-132.

Rayasam, G. et al., "Ligand-specific dynamics of the progesterone receptor in living cells and during chromatin remodeling in vitro ", Mol Cell (2005) Biol 25: 2406-2418.

Reddy, T. et al. "Genomic determination of the glucocorticoid response reveals unexpected mechanisms of gene regulation." (2009) Genome Res 19: 2163-2171.

(56) References Cited

OTHER PUBLICATIONS

Reich, M. et al. (2006) GenePattern 2.0. Nat Genet 38: 500-501.
Rezai et al., "A single-dose PK study of onapristone including the effect of food on absorption", Cancer Chemother. Pharmacol. (2015) 76: 171-177.
Rezai, K. et al., "Population pharmacokinetic (PPK) modeling of onapristone in patients (pts) with progesterone receptor (PR)-expressing cancers", AACR Annual Meeting (2015) Abstract 4523.
Richer, J. et al., "Differential gene regulation by the two progesterone receptor isoforms in human breast cancer cells." (2002) J Biol Chem 277: 5209-5218.
Robertson et al. "Onapristone, a progesterone receptor antagonist, as first-line therapy in primary breast cancer", (1999) vol. 35, Issue 2, pp. 214-218.
Final Office Action dated Oct. 24, 2019 U.S. Appl. No. 15/464,085.
Friedman, J. et al., "The Foxa family of transcription factors in development and metabolism." (2006) Cell Mol Life Sci 63: 2317-2328.
Garcia-Bassets, I. et al., "Histone methylation-dpendent mechanisms impose ligand dependency for gene activation by nuclear receptors." (2007) Cell 128: 505-518.
Goyeneche, A. et al., "Antiprogestins in gynecological diseases" Reproduction (2015) 149: RI5-R33.
Graham, D. et al., "Determination of the activated form of the progesterone receptor (PR) in endometrial cancer (EC)", J. Clin. Oncol. (2013); 3J (suppl; abstr 5602).
Graham, J. "Progesterone receptors—animal models and cell signaling in breast cancer Expression and transcriptonal activity of progesterone receptor A and progestereone receptor B in mamalian cells", Breast Cancer Res (2002) 4: 187-190.
Graham, J. et al., "Altered progesterone receptor isoform expression remodels progestin responsiveness of breast cancer cells." (2005) Mol Endocrinol 19: 2713-2735.
Graham, J. et al., "Characterization of progesterone receptor A and B expression in human breast cancer." (1995) Cancer Res 55: 5063-5068.
Graham, J. et al., "DNA replication licensing and progenitor numbers are increased by progesterone in normal human breast." (2009) Endocrinology 150: 3318-3326.
Graham, J. et al., "Expression and transcriptional activity of progesterone receptor A and progesterone receptor B in mammalian cells.", Breast Cancer Research (2002) 4(5): 187-190.
Graham, J. et al., "Physiological action of progesterone in target tissues." Endocr Rev (1997) 18: 502-519.
Grunberg et al., "Long-Term Administration of Mifepristone (RU486): Clinical Tolerance During Extended Treatment of Meningioma", Cancer Investigation, Jun. 11, 2009, 24:8, pp. 727-733.
Guohua et al., "Synthesis of Progesterone Receptor Antagonist ZK98299," Zhongguo Yaoke Daxue Xuebao (1992), 23 (4), 209-12.
Gwin K., et al., "Breast carcinoma with chondroid differentiations:a clinicopathologic study of 21 triple negative (ER-, PR-,Her2/neu-)cases." Int J Surg Pathol. (2010) 8 (1):27-35.
Hancock, B. et al., "Characteristics and Significance of the Amorphous State in Pharmaceutical Systems" Journal of Pharmaceutical Sciences (1997) vol. 88, No. I, pp. 1-12.
Heinz, S. et al., "Simple combinations of lineage-determining transcription factors prime cis-regulatory elements required for macrophage and B cell identities.", (2010) Mol Cell 38: 576-589.
Heydarzadeh et al., "Catalyst-free conversion of alkali cellulose to fine carboxymethyl cellulose at mild conditions", (2009) World Appl. Sci. J. 6 (4) 564-569.
Hopp, T. et al., "Breast Cancer Patients with Progesterone Receptor PR-A-Rich Tumors Have Poorer Disease-Free Survival Rates", Clin Cancer Res. (2004) 10; 2751.
Hubler, T. et al., "Intronic hormone response elements mediate regulation of FKBP5 by progestins and glucocorticoids." (2004) Cell Stress Chaperones 9: 243-252.
Hurtado, A. et al., "FOXA 1 is a key determinant of estrogen receptor function and endocrine response." (2011) Nat Genet 43: 27-33.
Hutt, E. et al., "Clinical and pathological correlation of the activated form of the progesterone receptor (APR) in Endometrial Cancer (EC)", ECC2013, 1.002.
Iasonos, A. et al., "Scientific Review of Phase I Protocols With Novel Dose-Escalation Designs: How Much Infomration is Needed?", J Clinical Oncology (2015) JCO.2014.59.8466.
International Search Report and Written Opinion dated Feb. 27, 2017 for International Patent Application No. PCT,US2016/066420.
International Search Report of International Patent Application No. PCT/US2012058732 dated Dec. 11, 2012.
International Application No. PCT/US2014/023651, Written Opinion dated Jul. 28, 2014, 11 pgs.
International Preliminary Report on Patentability issued in Internaional Patent Application No. PCT/IB2015/058369 dated May 2, 2017.
International Search Report and Written Opinion for International Patent Application No. PCT/US2017/023256 dated Jun. 16, 2017.
International Search Report and Written Opinion of PCT Application No. PCT/US2016/053435 dated Dec. 15, 2016.
International Search Report issued in International Patent Application No. PCT/IB2015/058369 dated Jan. 25, 2016.
International Search Report of corresponding PCT Application No. PCT/IB 2015/000312 dated Jul. 22, 2015.
International Search Report of PCT Application No. PCT/US2015/060940 dated Jan. 28, 2016.
Ishibashi, H. et al., "Progesterone receptor in non-small cell lung cancer—a potent prognostic factor and possible target for endocrine therapy", Cancer Res. (2005) 65 (14) 6450-8.
Jang et al, "Cytochrome P4503A4-Mediated N-Demethylation of the Antiprogestins Lilopristone and Onapristone", The American Society for Pharmacology and Experimental Therapeutics (1997) vol. 25, No. 10, 1119-1122.
Ji, H. et al., "An integrated software system for analyzing Ch IP-chip and ChIP-seq data." (2008) Nat Biotechnol 26: 1293-1300.
John, S. et al. "Chromatin accessibility pre-determines glucocorticoid receptor binding patterns.", (2011) Nat Genet 43: 264-268.
Jonat et al., "The clinical efficacy of progesterone antagonists in breast cancer", Endocrine Therapy of Breast Cancer, (2002) pp. 117-124.
Jonat, W. et al., "Randomized phase 2 study of lonaprisan as second line therapy for progesterone receptor positive breast cancer", Ann Oncol (2013) 24: 2543-2548.
Joseph, R. et al. "Integrative model of genomic factors for determining binding site selection by estrogen receptor-alpha." (2010) Mol Sys! Biol 6: 456.
Kamimura, H. et al., "Assessment of chimeric mice with humanized liver as a tool for predicting circulating human metabolites drug metab pharmacokinet", (2010) 25(3): 223-235.
Kao, L. et al., "Global gene profiling in human endometrium during the window of implantation." (2002) Endocrinology 143: 2119-2138.
Kawaguchi, Y. et al., "Drug and crystal polymorphism", Journal of Human Environmental Engineering, 2002, vol. 4, No. 2, p. 310-317.
Kim, J. et al., "Progesterone Action in Endometrial Cancer, Endometriosis, Uterine Fibroids, and Breast Cancer", Endocrine Rev. (2013) 34: 130-162.
Klijn et al., Progesterone antagonists and progesterone antagonist and progesterone receptor modulation in the treatment of beast cancer, (2000) Steroids, v. 65 pp. 825-830.
Knutson, et al., "Phosphorylated and sumoylation-deficient progesterone receptors drive proliferative gene signatures during breast cancer progession", Breast Cancer Research, 2012, vol. 14: R95.
Kocienski, Carbonyl Protecting Groups, 3rd Edition, Thieme (2005), pp. 58-59_.
Koivisto-Korander, R. "Mifepristone as treatment of recurrent progesterone receptor-positive uterine leiomyosarcoma", Obstetrics and Gynecology (2007) 109: 512-514.
Kojima, T., "To improve efficiency of selecting crystal shape with drug development", Journal of Pharmaceutical Science and Technology, (2008) vol. 68, No. 5, p. 344 349.
Krum, S. et al., "Unique ERalpha cistromes control cell type-specific gene regulation." (2008) Molecular Endocrinology 22: 2393-2406.

(56) References Cited

OTHER PUBLICATIONS

Kushner, P. et al., "Estrogen receptor pathways to AP-1." (2000) J Steroid Biochem Mol Biol 74: 311-317.

Lanari, C. et al., "Antiprogestins in breast cancer treatment: are we ready?", Endocrine-Related Cancer (2012) 19: R35-R50.

Roschke, A. et al., "Karyotypic complexity of the NCI-60 drug-screening panel." (2003) Cancer Res 63: 8634-8647.

Rossouw, J. et al., Risks and benefits of estrogen plus progestin in healthy postmenopausal women: principal results from the Women's Health Initiative randomized controlled trial. (2002) JAMA 288: 321-333.

Scarpin, K. et al., "Progesterone action in human tissues: regulation by progesterone receptor (PR) isoform expression, nuclear positioning and coregulator expression." (2009) Nucl Recept Signal 7: e009.

Schlogl S. et al., "Characteristics of the photochemical prevulcanization in a falling film photoreactor" J. App. Polymer Science, 2012, 124, 3478-3486.

Search Report of International Patent Application No. PCT/US2012/058732 dated Dec. 11, 2012.

Search Report of International Patent Application No. PCT/US2015/024792, dated Aug. 7, 2015.

Shi, et al., "Antigen retrieval immunohistochemistry under the influence of pH using monoclonal antibodies", Journal of Histochemistry & Cytochemistry (1995) vol. 43{2}, pp. 193-201.

So, A. et al., "Determinants of cell- and gene-specific transcriptional regulation by the glucocorticoid receptor." PLoS Genetics (2007) vol. 3, Issue 6; 0927-0938.

Streuli, C. et al., "Stat5 as a target for regulation by extracellular matrix.", (1995) J Biol Chem 270: 21639-21644.

Tang, Q. et al., "A comprehensive view of nuclear receptor cancer cistromes." (2011) Cancer Res 71: 6940-6947.

Telleria et al., "Antiprogestins in Ovarian Cancer. Ovarian Cancer—Clinical and Therapeutic Perspectives, DOI: 10.5772/25269", (2012) 207-230.

Thike et al., "Triple-negative breast cancer; clnicopathological characteristics and relationship with basal-like breast cancer," Modern Pathology, 2010; 23; pp. 123-133.

Tseng, L. et al., "Progesterone receptor (hPR) upregulates the fibronectin promoter activity in human decidual fibroblasts." (2003) DNA Cell Biol 22: 633-640.

Vicent, G. et al., "Chromatin remodeling and control of cell proliferation by progestins via cross talk of progesterone receptor with the estrogen receptors and kinase signaling pathways." (2006) Ann N Y Acad Sci 1089: 59-72.

Vicent, G. et al., "Minireview: role of kinases and chromatin remodeling in progesterone signaling to chromatin." Mol Endocrinol (2010) 1-11.

Vicent, G. et al., "Two chromatin remodeling activities cooperate during activation of hormone responsive promoters." PLoS Genet (2009) vol. 5, Issue 7: 1-13.

Vicent, G. et al., Nuclear factor 1 synergizes with progesterone receptor on the mouse mammary tumor virus promoter wrapped around a histone H3/H4 tetramer by facilitating access to the central hormone-responsive elements. (2010) J Biol Chem 285: 2622-2631.

Wang, D. et al. "Reprogramming transcription by distinct classes of enhancers functionally defined by eRNA." Nature (2011) 1-25.

Wang, Q. et al., A hierarchical network of transcription factors governs androgen receptor-dependent prostate cancer grow1h. (2007) Mol Cell 27: 380-392.

Welboren, W. et al., "ChIP-Seq of ERalpha and RNA polymerase II defines genes differentially responding to ligands." (2009) EMBO J 28: 1418-1428.

Wizinger et al., Triphenymethanfarbstoffe aus Thiodiphenylamin undPhenoxazin, Helvetica Chimica Acta, (1952) vol. 35, pp. 316-329.

Written Opinion for PCT/US2017/023256, dated Jun. 16, 2017.

Written Opinion issued in International Patent Application No. PCT/IB2015/058369 dated Jan. 25, 2016.

Written Opinion of International Patent Application No. PCT/US2012/058732, dated Dec. 11, 2012.

Yamano, M., "Approach to Crystal Polymorph in Process Research of New Drug", Journal of Synthetic Organic Chemistry, (2007) vol. 65, No. 9, p_ 907(69)-913(75).

Yin, P. et al. "Genome-wide progesterone receptor binding: cell type-specific and shared mechanisms in T47D breast cancer cells and primary leiomyoma cells." (2012) PLoS One 7: e29021.

Yin, P. et al., "Transcription Factor KLFI 1 Integrates Progesterone Receptor Signaling and Proliferation in Uterine Leiomyoma Cells", Cancer Res (2010) 70(4); 1722-30.

Zala et al., "Laboratory Techniques of purification and isolation", Int. J. Drug Dev. & Res., (2012) vol. 4, No. 2, pp. 41-155.

Zukiwski et al., "Independent characterization by duel staining of progesterone receptor (PR) and estrogen receptor (ER) in breast cancer (BC)", Proc ASCO, abstract No. 118076 (2003).

* cited by examiner

Onapristone $C_{max}$ vs Dose

Regimen = 50 mg bid

Regimen = 100 mg QD

ONAPRISTONE EXTENDED-RELEASE COMPOSITIONS AND METHODS

PRIORITY CLAIM

This application is a continuation of U.S. patent application Ser. No. 14/942,809, filed Nov. 16, 2015, which claims the benefit of U.S. Provisional Patent Application Ser. No. 62/080,868 filed Nov. 17, 2014, each of which is hereby incorporated by reference in its entirety.

BACKGROUND

Onapristone (ONA) is an anti-progestin drug and progesterone receptor antagonist which was originally developed for potential contraceptive use and the use in benign gynecological disorders such as the treatment of uterine leiomyomas. However, onapristone has demonstrated substantial activity in advanced breast cancer. It is thought that ONA binds to the progesterone receptor (PR), preventing the PR from binding to DNA and thereby inhibiting or eliminating PR-induced DNA transcription. See, e.g., Klijn et al., Progesterone antagonists and progesterone receptor modulation in the treatment of breast cancer, Steroids, v. 65, pp. 825-830 (2000); Jonat et al., The clinical efficacy of progesterone antagonists in breast cancer, Endocrine Therapy of Breast Cancer, pp. 117-124.

Onapristone is a type I progesterone receptor (PR) antagonist, which prevents PR-induced DNA transcription. Presence of transcriptionally activated PR (APR) in tissue samples from a cancer patient, measured using, for example, an immunohistochemistry companion diagnostic procedure, indicates susceptibility to treatment with onapristone anti-cancer activity. Onapristone anti-cancer activity is documented in multiple pre-clinical models and clinical studies in patients with hormone therapy-naive or tamoxifen-resistant breast cancer. Despite promising activity in breast cancer models, the development of onapristone as an oncology drug was terminated due to liver function test abnormalities. See, e.g., Robertson et al., Eur J Cancer. 35(2): 214-8 (February 1999).

Expression of the progesterone receptor (PR) has been described in breast [Mote 2000, Lange 2008], endometrial [Kim 2013, Mortel 1984], prostate [Lange 2007, Bonkhoff 2001], ovarian [Sieh 2013], and several other cancers [Yin 2010, Ishibashi 2005, Blankenstein 2000]. Antiprogestins have been shown to have an inhibitory effect on the growth of different type of cancer cells, and antiprogestin treatment has been studied in breast [Jonat 2013], endometrial [Thigpen 1999], prostate [Taplin 2008] cancers and uterine sarcomas [Koivisto-Korander 2007].

The effects of progesterone are mediated by two distinct nuclear receptor proteins, PRA and PRB, two transcriptional isoforms of the single PR gene. In luminal epithelial cells of the normal breast and in normal endometrium, both PR isoforms are expressed and are required to mediate the physiological effects of progestin ligands [Mote 2002, Arnett-Mansfield 2004]. The two PR isoforms have both been detected in malignant tissues, such as breast, endometrial, ovarian and prostate cancers [Cottu 2015].

ONA is a type I antiprogestin which prevents PR monomers from dimerizing, inhibits ligand-induced phosphorylation, prevents association of the PR with its co-activators, and thus prevents PR-mediated DNA transcription. ONA does not allow the PR complex to bind to DNA, does not or minimally modulates PR-mediated genes, and inhibits ligand-induced PR phosphorylation, in contrast to other antiprogestins [Beck 1996; Afhüppe 2009]. Preclinical activity has been shown in several models, including endometrial cancer [Mueller 2003] and the clinical anticancer activity of ONA has been previously documented in patients with hormone therapy-naive [Robertson 1999] or tamoxifen-resistant [Jonat 2002] breast cancer.

Transcriptionally activated PR (APR) can be detected by observational evaluation of the subnuclear distribution pattern using immunohistochemistry (IHC). Using this method, APR can be used as a potentially predictive IHC biomarker in endometrioid cancer of the uterus. Se, U.S. Pat. No. 9,046,534. APR detection is being developed as a companion diagnostic to identify patients more likely to respond to ONA [Bonneterre 2015].

Early clinical studies employing the original immediate release (IR) formulation of ONA have shown that ONA is well-tolerated with the exception of abnormalities in liver function tests (LFTs) [Cameron 1996, Cameron 2003, Croxatto 1994, Jonat 2002, Robertson 1999]. Studies with the original IR formulation were discontinued due to these LFT abnormalities. Id.

Previously, onapristone was provided to patients with cancer (e.g., breast, endometrial, others) in an immediate release formulation of 100 mg and provided QD (once per day). Onapristone has also been given to patients in endocrinology studies, at immediate release doses of 1 and 10 mg doses resulting in a dose-dependent effect of onapristone on suppression of gonadotrophin (luteinizing hormone [LH] and follicle-stimulating hormone [FSH]) secretion. Cameron 2003. However, these studies used immediate release formulations of onapristone of unknown purity. Importantly, these studies addressed the dose and formulation of onapristone suitable for potential contraceptive use rather than the dose and formulation suitable for treating a disease such as cancer.

What is needed is an improved formulation of onapristone which allow for a continuous suppression of the PR and methods of administering the same resulting in sufficient bioavailability to provide clinical benefit to cancer patients at doses which result in less toxicity than the previous clinical experience with onapristone.

SUMMARY

Aspects described herein provide extended-release pharmaceutical compositions comprising onapristone as the active ingredient in an amount from about 2 mg to about 100 mg. The extended-release pharmaceutical compositions (also referred to herein as ER formulations) further comprise excipients suitable for the desired dosage form (e.g., tablet, capsule, etc.) and for delaying the release of the active ingredient.

Further aspects provide onapristone ER formulations utilizing highly purified onapristone (e.g., at least about 98%). In another aspect, the ratio of onapristone to inactive excipients in the ER formulations is about 0.05 to about 5%.

In a further aspect, the AUC (area under the curve) of onapristone is at least about 1578 ng*h/ml over about an 8-12 hour period after administration of a 10 mg dose BID (i.e., twice per day) to a patient.

In another aspect, the Cmax (maximum plasma concentration) of onapristone is at least about 240 ng/ml over about an 8-12 hour period after administration of a 10 mg dose BID to a patient. In yet another aspect, a steady state plasma concentration of onapristone is achieved at about 8 days following the initial dose of the extended release onapristone pharmaceutical composition. In another aspect, the extended-release onapristone pharmaceutical composition comprises at least about 10 mg to about 50 mg of onapristone.

DETAILED DESCRIPTION

Figure 1:
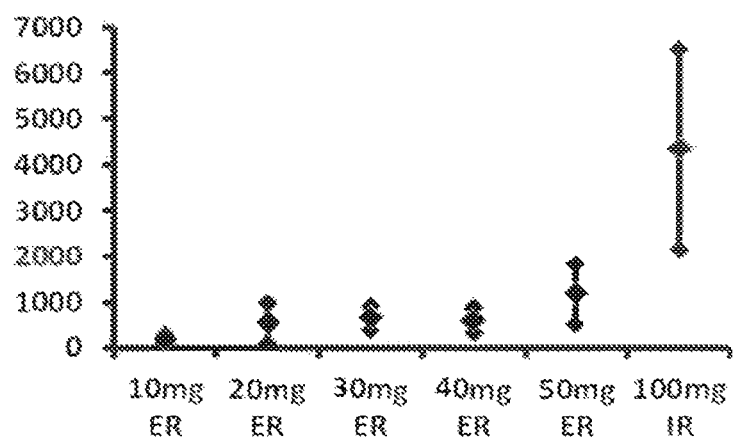
FIG. 1 shows the exemplary Cmax (maximum active ingredient concentration) levels per ONA dose level (10 mg, 20 mg, 30 mg, 40 mg, 50 mg extended-release BID (twice per day) and 100 mg QD (once per day))

Before describing several exemplary aspects described herein, it is to be understood that the invention is not limited to the details of construction or process steps set forth in the following description. The aspects described herein are capable of being practiced or being carried out in various ways.

In another aspect onapristone ER formulations comprise onapristone (ONA) ((8S,11R,13R,14S,17S)-11-[4-(dimethylamino)phenyl]-17-hydroxy-17-(3-hydroxypropyl)-13-methyl-1,2,6,7,8,11,12,14,15,16-decahydrocyclopenta[a]phenanthren-3-one), an anti-progestin drug and progesterone receptor antagonist having the following structure:

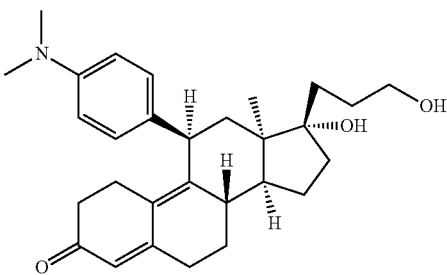

In one aspect, ER formulations of onapristone are provided. The term "extended release" refers to a pharmaceutical compositions or drug formulation that is administered to a patient and has a mechanism to delay the release an active ingredient (i.e., drug). For example, ER pharmaceutical compositions include the active ingredient (e.g., onapristone) and excipients that delay release of the active ingredient (e.g., hydroxypropyl methylcellulose, ethyl cellulose, Eudragit● (Evonik Industries) sustained release formulations (polymethacrylates), polyvinylpyrrolidone (PVP), carrageenan, etc.). The term "immediate release" (IR) refers to pharmaceutical compositions or drug formulations that do not have a mechanism for delaying the release of the active ingredient following administration of the formulation to a patient. Exemplary extended release formulations are provided, for example, in Table 4 herein. The terms "treat," "prevent," or similar terms, as used herein, do not necessarily mean 100% or complete treatment or prevention. Rather, these terms refer to various degrees of treatment or prevention of a particular disease (e.g., 100%, 90%, 80%, 70%, 60%, 50%, 40%, 30%, 20%, 10%, 5%, or 1%) as recognized in the art as being beneficial. The terms "treatment" or "prevention" also refer to delaying onset of a disease for a period of time or delaying onset indefinitely. The term "treatment" or "treating" refers to administering a drug or treatment to a patient or prescribing a drug to a patient where the patient or a third party (e.g., caretaker, family member, or health care professional) administers the drug or treatment One aspect provides an extended-release pharmaceutical composition comprising onapristone wherein onapristone is present in an amount from about 2 mg to about 50 mg. Onapristone can be provided, for example, in quantities of 2 mg, 2.5 mg, 5 mg, 10 mg, 20 mg, 25 mg, 37.5 mg, and 50 mg in any suitable extended release formulation (e.g., formulations of Table 4) multiple times per day (e.g., twice per day) or once per day. ER formulations can include excipients that delay the dissolution of the tablet and the subsequent release of onapristone into the gastrointestinal track which then is absorbed into the bloodstream of a patient over time thereby reducing the $C_{max}$ concentration compared to an IR formulation. A similar release profile can be achieved through the use of an osmotic tablet or a tablet film coated with a polymer that results in an extended release profile of the tablet.

In another aspect, onapristone ER formulations can be provided in any suitable dosage form (e.g., tablet, capsule, etc.) with a total weight of active ingredients plus excipients ranging from about 50 mg to 400 mg. In another aspect, the tablet can be a matrix tablet, film coated tablet or osmotic pump. In yet another aspect, onapristone ER formulations can be administered to a patient in need of treatment with onapristone once per day, twice per day (BID), or more to achieve the desired dose of onapristone.

Further aspects provide onapristone ER formulations wherein the purity of the onapristone is at least about 98%. Without being bound by theory, it is believed that using a highly purified form of onapristone in part decreases the liver function test abnormalities resulting in clinical benefits for cancer patients at all doses.

In another aspect, the ratio of onapristone to inactive excipients in the onapristone ER formulation is about 0.05 (e.g., Table 4) to about 5%.

Further aspects provide ER formulations wherein the AUC of onapristone following the administration of 10 mg of the onapristone ER formulation to a patient BID is at least about 1578 ng*h/ml over about 8-12 hours. In one aspect, the time period can vary by about plus or minus two hours.

Another aspect provides onapristone ER formulations where the Cmax of onapristone following the administration of 10 mg of the onapristone ER formulation to a patient BID is at least about 240 ng/ml over about 8-12 hours. In one aspect, the time period can vary by about plus or minus two hours.

Another aspect provides onapristone ER formulations where a steady state plasma concentration of onapristone is achieved at about 8 days following the administration of the onapristone ER formulations to a patient twice a day (BID).

Further aspects provide methods of administering onapristone to a patient comprising administering an onapristone ER formulation twice per day (BID) to a cancer patient, where the onapristone ER formulation comprises of at least about 10 mg to about 50 mg of onapristone. In one aspect, the ER formulation is administered once per day. In another aspect, the onapristone in the onapristone ER formulation is at least about 98% pure.

In one aspect, the onapristone administered to a patient it at least about 98% pure. In yet another aspect, onapristone in the onapristone ER formulations can be provided, for example, in quantities of 2 mg, 2.5 mg, 5 mg, 10 mg, 20 mg, 25 mg, 37.5 mg, and 50 mg.

In yet another aspect, the onapristone ER formulations can be administered twice per day (BID) to a human subject in need of treatment, where the onapristone ER formulation comprises of at least about 10 mg to about 50 mg of onapristone. In one aspect, the ER formulation is administered once per day. In another aspect, the disorder is selected from the group consisting of breast cancer, endometrial cancer, prostate cancer, ovarian, uterine endometrioid cancers, and other types of cancer which express the PR.

In another aspect, the onapristone ER formulation is administered to a human subject having a disorder capable of treatment with onapristone wherein the the AUC of onapristone following the administration of 10 mg of the onapristone ER formulation to a patient BID is at least about 1578 ng*h/ml over about 8-12 hours. In another aspect, the time period can vary by about plus or minus two hours.

In another aspect, the onapristone ER formulation is administered to a human subject having a disorder capable of treatment with onapristone by administering an onapristone ER formulation to the subject twice per day (BID) where the Cmax of onapristone in the human subject is at least about 240 ng/ml over about 8-12 hours. In another aspect, the onapristone ER formulation is administered once per day. In yet another aspect, the time period can vary by about plus or minus two hours.

In another aspect, an onapristone ER formulation is administered to a human subject having a disorder capable of treatment with onapristone twice per day (BID) where a steady state plasma concentration is achieved at about 8 days.

Figure 2:
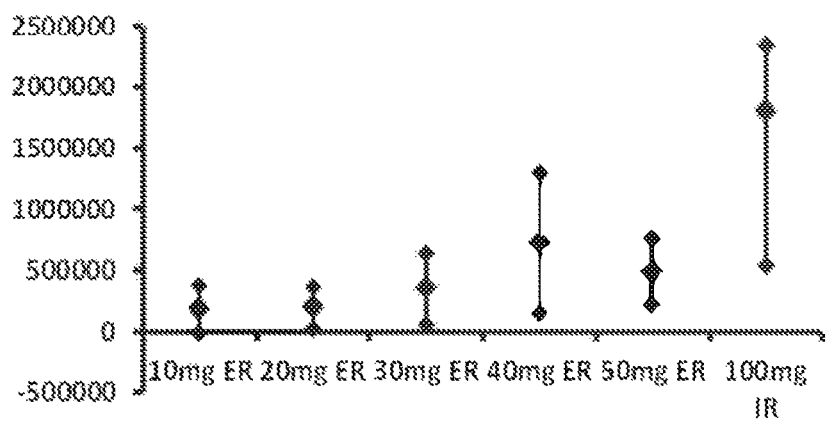
FIG. 2 shows the exemplary AUC (area under the curve) per ONA dose level (10 mg, 20 mg, 30 mg, 40 mg, 50 mg extended-release formulations BID (twice per day) and 100 mg QD (once per day))

PK results for onapristone are available for 52 patients from the a first study (ARN-AR18-CT-101) (Table 1). Variability for onapristone PK is moderate and greater for the IR versus the ER formulation. Onapristone Cmax and AUC values for the ER form are proportional to administered dose (FIGS. 1 and 2). Based on observed mean AUC values, oral bioavailability for the ER versus the IR formulation is approximately 50% (FIG. 24). A later Tmax value for the ER form results in somewhat lower dose-corrected Cmax values for the ER form compared to the IR form. Steady state is attained before day 8 with a mean t % of 7.5 hrs.

Table 1 compares descriptive statistics for the primary onapristone pharmacokinetic exposure parameters following single oral doses from 10 to 50 mg of extended-release onapristone compared to that from 100 mg immediate-release onapristone (Study ARN-AR18-CT-101). Exposure following ER onapristone appears later than that for IR onapristone, consistent with extended release formulations. However, the extended-release aspects are not reflected in the overall duration of exposure. Although study size is small, onapristone exposure generally increases in proportion to ER onapristone dose. Exposure at 50 mg ER onapristone is approximately 20-50% that of 100 mg IR onapristone depending on the formulation. Variability in these parameters is similar for both formulations and across ER onapristone dose levels.

TABLE 1

Summary of PK results for 52 Patients From Study ARN-AR18-CT-101

| | Form | | | | | |
|---|---|---|---|---|---|---|
| | ER | ER | ER | ER | ER | IR |
| | | | Dose (mg) | | | |
| | 10 | 20 | 30 | 40 | 50 | 100 |
| | | | n | | | |
| | 12 | 12 | 6 | 10 | 6 | 6 |
| | | | $AUC_{tau}$ (ng*h/mL) | | | |
| Mean | 1578 | 4228 | 4856 | 6833 | 8966 | 40800 |
| CV % | 75 | 94 | 19 | 65 | 53 | 51 |
| | | | $C_{max}$ (ng/mL) | | | |
| Mean | 240 | 586 | 767 | 870 | 1459 | 4296 |
| CV % | 67 | 77 | 15 | 67 | 48 | 54 |
| | | | $t_{max}$ (hrs) | | | |
| Mean | 3.4 | 3.8 | 3.8 | 5.2 | 2.5 | 1.3 |
| CV % | 47 | 50 | 51 | 68 | 55 | 61 |
| | | | $t_{1/2}$ (hrs) | | | |
| Mean | 8.9 | 7.9 | 3.9 | 23.9 | 11.1 | 23.6 |
| CV % | 120 | 39 | 31 | 183 | 140 | 165 |

PK results are available in 19 patients from a second study (ARN-AR18-CT-102) and show linear dose relationships for $C_{max}$ and AUC (Table 2) following single oral doses from 10 to 50 mg of extended-release onapristone. Confirming the ARN-AR18-CT-101 study, the ER formulation appears to be performing according to the dose release specifications with a $t_{1/2}$ of approximately 8 hours and a $T_{max}$ of approximately 3-4 hours. Steady state is also achieved within 8 days in this study. Day 29 and 57 data indicate no evidence of accumulation over time, once steady state is reached. Onapristone exposure generally increases less than proportionally with the ER onapristone dose formulation. Variability in these parameters is similar across ER onapristone dose levels.

TABLE 2

Summary of PK results for 19 Patients From Study ARN-AR18-CT-102

| | Onapristone ER twice-daily dose | | | | |
|---|---|---|---|---|---|
| Parameter mean (CV %) | 10 mg n = 5 | 20 mg n = 5 | 30 mg n = 3 | 40 mg n = 3 | 50 mg n = 3 |
| $T_{max}$, h | 4.0 (43) | 3.6 (46) | 4.0 (50) | 3.0 (88) | 3.3 (35) |
| $C_{max}$, ng/mL | 260 (51) | 362 (41) | 325 (62) | 680 (14) | 538 (44) |
| $AUC_i$, ng/mL * h | 7013 (53) | 9745 (44) | 14380 (18) | 17300 (27) | 23541 (39) |
| CL, L/h | 1.85 (48) | 2.04 (31) | 2.13 (18) | 2.18 (10) | 2.4 (46) |
| $t_{1/2}$, h | 5.46 (63) | 5.61 (30) | 9.46 (44) | 5.45 (55) | 15.9 (53) |

FIGS. 1 and 2 show the results of an exemplary comparison of the relative systemic onapristone exposure following single oral doses from 10 to 50 mg of extended release onapristone compared to that from 100 mg immediate-release onapristone (Study ARN-AR18-CT-101). Onapristone exposure, assessed by Cmax (FIG. 1) and AUC (FIG. 2), increases linearly across the ER onapristone dose range and is lower than that for IR onapristone at all ER dose levels. Surprisingly, as disclosed herein, the ER onapristone formulations provided clinical benefit to patients despite lower onapristone exposure.

Figure 3:
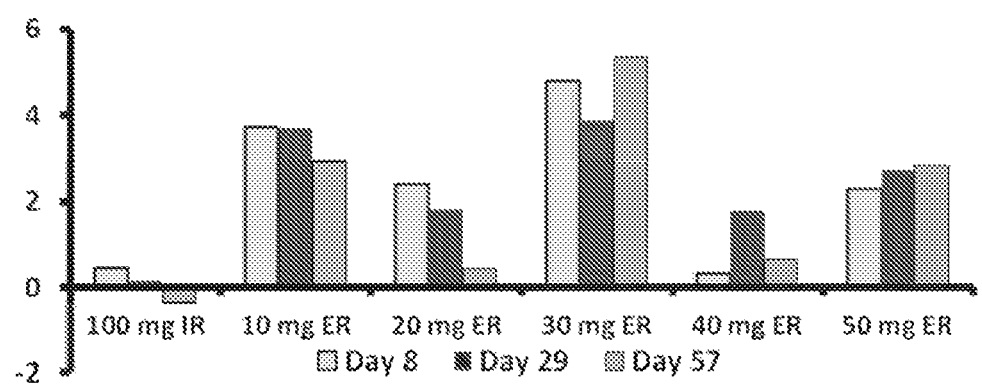
FIG. 3 shows the exemplary accumulation of ONA over time per ONA dose level (10 mg, 20 mg, 30 mg, 40 mg, 50 mg extended-release formulations BID (twice per day) and 100 mg QD (once per day))

FIG. 3 shows the results of an exemplary comparison of the degree of onapristone accumulation following twice-daily oral doses from 10 to 50 mg of extended-release onapristone compared to that from daily oral 100 mg immediate-release onapristone (Study ARN-AR18-CT-101). Accumulation for the ER onapristone formulation given twice daily is measurably greater than that for IR onapristone given daily.

Figure 4A:
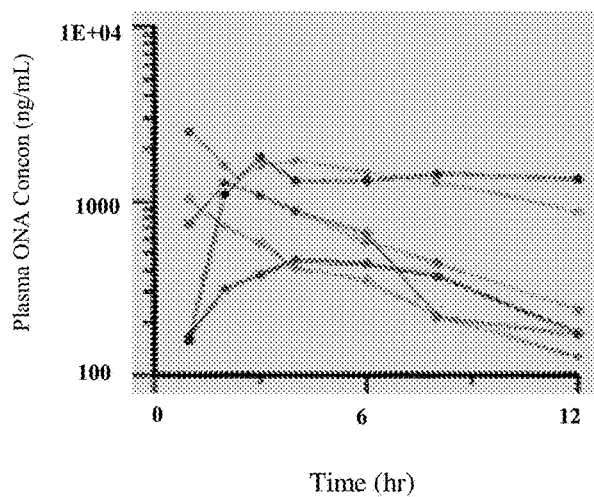
FIGS. 4A and 4B show exemplary ONA plasma levels over time per dose levels for the extended-release formulations BID (FIG. 4A) and the 100 mg formulation QD.
Figure 4B:
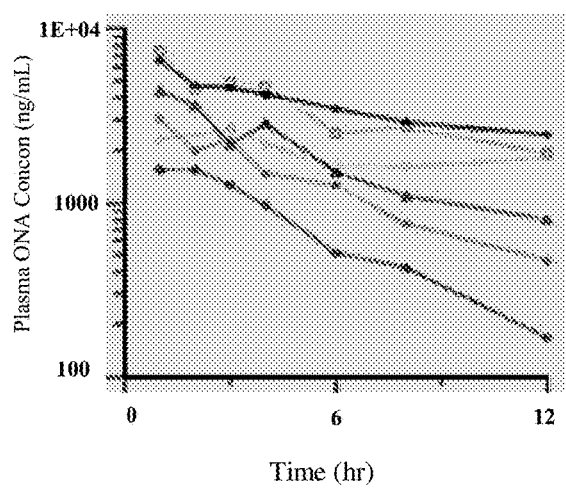

FIGS. 4A and 4B show exemplary plasma onapristone concentration-time profiles for individual subjects following single oral doses of 50 mg extended-release onapristone compared to that from 100 mg immediate-release onapristone (Study ARN-AR18-CT-101). The profiles for ER onapristone generally reach maximum concentrations more slowly than those for IR onapristone, supporting the extended release of drug from the ER formulation. Concentrations at all dose levels of ER onapristone are generally lower than those for 100 mg IR onapristone. Surprisingly, as disclosed herein, the ER onapristone formulations provided clinical benefit to patients despite lower onapristone exposure.

TABLE 3

Efficacy In Study ARN-AR18-CT-101

| Tumor type | Dose | Response | % change STL | Duration weeks |
|---|---|---|---|---|
| Serous OC | 10 | PR | −52 | 40 |
| Serous OC | 50 | SD | −7 | 34 |
| Granulosa OC | 40 | SD | −24 | 24 |
| Granulosa OC | 30 | SD | +5 | 32 |
| EC | 30 | SD | −13 | 30+ |
| EC | 20 | SD | +5 | 32 |
| BC | 50 | SD | −7 | 32+ |
| BC | 20 | SD | NA | 28 |
| BC | 40 | SD | −10 | 24 |

Clinical benefit (PR (partial response or SD (stable disease) for ≥24 weeks) was observed in ovarian, breast and uterine endometrioid cancers using the onapristone ER formulation. One patient with serous ovarian cancer experienced a PR (32 week duration) and 8 patients had SD for at least 24 weeks (Table 3). The median progression free survival (PFS) was 57.5 days (range 21-281).

In study ARN-AR18-CT-101, in 52 female patients with PR-positive solid tumors, 9/46 patients (20%) receiving the onapristone ER formulation at doses from 10-50 mg BID demonstrated clinical benefit, vs. 0/6 (0%) patients receiving the 100 mg once-daily onapristone IR formulation. Clinical benefit responses, defined as RECIST 1.1 partial response or stable disease for at least 24 weeks, were seen only in patients receiving ER. Of interest, 7/9 of the patients with clinical benefit (78%) received doses below the established 100 mg IR dose and the patient with a partial response was treated at the lowest ER dose level, 10 mg BID.

With respect to ARN-AR18-CT-102, 2 of 21 patients with prostate cancer had SD after week 12. Median duration of treatment was 8 weeks.

EXAMPLES

The following non-limiting examples illustrate aspects described herein. Not every element described herein is required. Indeed, a person of skill in the art will find numerous additional uses of and variations to the methods described herein, which the inventors intend to be limited only by the claims. All references cited herein are incorporated by reference in their entirety.

Example 1

ER Formulations

TABLE 4

Onapristone Extended-Release Formulations

| | Amount per tablet (mg) | | | | |
|---|---|---|---|---|---|
| Component | 2.5 mg | 5 mg | 10 mg | 20 mg | Function |
| Onapristone | 2.50 | 5.00 | 10.00 | 20.00 | Active |
| Lactose monohydrate | 10.25 | 20.50 | 41.00 | 82.00 | Filler |
| Microcrystalline cellulose | 10.25 | 20.50 | 41.00 | 82.00 | Filler |
| Pregelatinized starch | 10.00 | 20.00 | 40.00 | 80.00 | Disintegrant |
| Hydroxypropyl methylcellulose | 16.50 | 33.00 | 66.00 | 132.00 | Binder/modified release agent |
| Colloidal silicon dioxide | 0.25 | 0.50 | 1.00 | 2.00 | Glidant |
| Magnesium stearate | 0.25 | 0.50 | 1.00 | 2.00 | Lubricant |
| Tablet weight (mg) | 50.00 | 100.00 | 200.00 | 400.00 | |

Table 4 provide exemplary onapristone extended release formulations. In one aspect, the tablets can be provided to a patient alone or in any desired combination to achieve the desired dose.

Example 2—Preparing Exemplary Onapristone ER Formulations

Onapristone extended-release formulations can be prepared by the following exemplary method:

Step 1: De-lump onapristone drug substance by milling or by passing through a wire screen followed by further passing the resulting de-lumped onapristone through a wire screen of appropriate mesh size (e.g., 425 or 710 microns).

Step 2: Screen the colloidal silicon dioxide and approximately half of the pregelatinized starch separately through a screen of appropriate mesh size (e.g., 425 or 710 microns) into a stainless steel blending container. The previously-screened onapristone drug substance from Step 1 is added to this blend.

Step 3: The mixture is blended and screened through a screen of appropriate mesh size (e.g., 425 or 710 microns).

Step 4: The remaining pregelatinized starch is screened through a screen of appropriate mesh size (e.g., 425 or 710 microns) into the stainless steel blending container (from Step 2). The previously screened mixture from Step 3 is added to the container.

Step 5: The mixture is blended to achieve a homogenous mix.

Step 6: Approximately half of the microcrystalline cellulose, half of the lactose monohydrate and half of the hydroxypropyl methylcellulose are separately screened into a larger stainless steel blending container through a screen of appropriate mesh size (e.g., 425 or 710 microns). The blend from Step 5 is added to this container, and the remaining microcrystalline cellulose, lactose monohydrate and hydroxypropyl methylcellulose are screened into the container through a screen of appropriate mesh size (e.g., 425 or 710 microns).

Step 7: The mixture is blended further to achieve a homogeneous mix.

Step 8: The mixture from Step 7 is co-screened with magnesium stearate through a screen of appropriate mesh size (e.g., 425 or 710 microns) into the container from Step 4.

Example 3

Patients and Methods
Eligibility
Inclusion Criteria Included:

(1) post-menopausal female patients≥18 years of age that have been previously treated recurrent or metastatic progesterone receptor-expressing cancer (e.g., endometrial, ovarian, breast cancer or uterine sarcoma) with evaluable disease per Response Evaluation Criteria In Solid Tumors, version 1.1 (RECIST 1.1);

(2) patients having available tissue blocks or biopsy specimens to determine progesterone receptor (PR) and activated progesterone receptor (APR) status; and (3) patients having Eastern Cooperative Oncology Group (ECOG) performance status 0-1, and signed informed consent.

The PR determination for inclusion purposes was performed on archived tissue blocks in the pathology department of each participating center. Central PR/APR evaluation was planned, but retrospective relative to inclusion and treatment.

Key exclusion criteria included significantly impaired liver or kidney function, creatinine clearance lower than 60 mL/min, total bilirubin>upper limit of normal (ULN), alkaline phosphatase>ULN (or >2.5×ULN with liver or >5×ULN with bone metastases), ALT/AST>ULN (or >2.5× ULN with liver metastases), QTcF>480 msec, chronic inflammatory liver condition, severe concomitant disease, uncontrolled brain metastases, inadequate washout from previous therapy, inability to swallow or absorb tablets, use of inhibitors, inducers or substrates of CYP3A4, or use of progestin-based hormone replacement therapy.

Example 4

Study Design and Treatment

The study was an open-label, multicenter, randomized, parallel-group, two part phase 1-2 study with phase I part of the trial discussed herein. To determine the recommended phase 2 dose (RP2D), patients enrolled in this phase 1 study were randomized in parallel fashion to six (6) cohorts: five (5) cohorts of ER ONA tablets (10 mg BID, 20 mg BID, 30 mg BID, 40 mg BID, 50 mg BID) and one (1) cohort using the IR tablet formulation (100 mg QD). The trial was conducted in five (5) centers in France (registered on ClinicalTrials.gov as NCT02052128).

The study was approved by the Ile de France III Comité pour la Protection des Personnes (a French national ethics committee), the ANSM (French regulatory authority) and individual site scientific review boards, and written informed consent was obtained from each study patient.

Highly purified ONA tablets can be by standard pharmaceutical chemistry purification methods by those skilled in the art. ER formulation with release kinetics from 10-12 hours depending on tablet dose. The original study design included a 20-patient expansion component. An 8-week dose-limiting toxicity (DLT) observation period was utilized to characterize thoroughly the safety profile, as previous ONA studies demonstrated a spike in the LFTs at approximately 6 weeks of treatment.

Patients were treated until documented progressive disease (PD) or intolerance to medication. We consider the design of this study to be in agreement with the recently-proposed guidance for phase 1 protocols for dose escalation [Iasonos 2015].

Example 5

Pharmacokinetics Methods

Blood samples were collected at 0, 1, 2, 3, 4, 6, 8, 12 (before next BID dose), and 24 (before next dose—for 100 mg IR only) hours post-ONA, as well as hour 0 on days 8, 29 and 57 (just before drug intake). Plasma concentrations of ONA, mono-demethylated onapristone (M1) and other metabolites in plasma and urine were analyzed with a validated ultra-performance liquid chromatography with tandem mass spectrometry detection (UPLC-MS/MS) assay. Pharmacokinetic modeling was performed using Monolix software in order to estimate PK parameters Cmax, Tmax, AUC0-last, AUC0-8, t1/2, Vd, CL, and Vc.

Although the above description refers to particular aspects, it is to be understood that these aspects are merely illustrative. It will be apparent to those skilled in the art that various modifications and variations can be made to the polymorphic forms and methods described herein. Thus, it is intended that the present description include modifications and variations that are within the scope of the appended claims and their equivalents.

REFERENCES

1. Afhiippe W, Sommer A, Muller J et al. Global gene expression profiling of progesterone receptor modulators in T47D cells provides a new classification system. J Steroid Biochem Mol Biol 2009; 113:101-115.
2. Arnett-Mansfield R L, DeFazio A, Mote P A et al. Sub-nuclear Distribution of Progesterone Receptors A and B in Normal and Malignant Endometrium. The Journal of Clinical Endocrinology & Metabolism 2004; 89: 1429-1442.
3. Beck C A, Zhang Y, Weigel N et al. Two Types of Anti-progestins Have Distinct Effects on Site-specific Phosphorylation of Human Progesterone Receptor. The Journal of Biological Chemistry 1996; 271:1209-1217.
4. Benagiano G, Bastianelli C, Farris M. Selective progesterone receptor modulators 3: use in oncology, endocrinology and psychiatry. Expert Opin. Pharmacother 2008; 9:2487-2496.
5. Blankenstein M A, Verheijen F M, Jacobs J M et al. Occurrence, regulation, and significance of progesterone receptors in human meningioma. Steroids 2000; 65: 795-800

6. Bonkhoff H, Fixemer T, Hunsicker I, and Remberger K. Progesterone Receptor Expression in Human Prostate Cancer: Correlation With Tumor Progression. Prostate 2001; 48:285-291.
7. Bonneterre J, Hutt E, Bosq J et al. Development of a technique to detect the activated form of the progesterone receptor and correlation with clinical and histopathological characteristics of endometrioid adenocarcinoma of the uterine corpus. Gynecologic Oncology 2015; doi: 10.1016/j.ygyno.2015.06.037
8. Cameron S, Critchley H O D, Buckley C H et al. The effects of post-ovulatory administration of onapristone on the development of a secretory endometrium. Human Reproduction 1996; 11 (1):40-49.
9. Cameron S T, Glasier A F, Narvekar N et al. Effects of onapristone on postmenopausal endometrium. Steroids 2003; 68:1053-1059.
10. Cottu P, A Italiano, A Varga et al. Onapristone (ONA) in progesterone receptor (PR)-expressing tumors: Efficacy and biomarker results of a dose-escalation phase 1 study. J Clin Oncol 2015; 33 (suppl; abstr 5593).
11. Croxatto H, Salvatierra A A, Fuentealba B et al. Effect of the antiprogestin onapristone on follicular growth in women. Human Reproduction 1994; 9: 1442-1447.
12. Goyeneche A A and Telleria C M. Antiprogestins in gynecological diseases. Reproduction 2015 149: R15-R33.
13. Graham D, Bosq J, Caillaud J M et al. Determination of the activated form of the progesterone receptor (PR) in endometrial cancer (EC). J Clin Oncol 2013; 31(suppl; abstr 5602).
14. Hopp T A, Weiss H L, Hilsenbeck S G, et al. Breast Cancer Patients with Progesterone Receptor PR-A-Rich Tumors Have Poorer Disease-Free Survival Rates. Clin Cancer Res 2004 10; 2751
15. Hutt E, Bosq J, Powell M A, Leblanc E, Fujiwara K, Herzog T J, Coleman R L, Graham D, Clarke C, Gilles E M, Zukiwski A A, Monk B J. Clinical and pathological correlation of the activated form of the progesterone receptor (APR) in Endometrial Cancer (EC). ECC 2013, #1.002
16. Iasonos A, Gönen M, Bosl G J. Scientific Review of Phase I Protocols With Novel Dose-Escalation Designs: How Much Information Is Needed? Journal of Clinical Oncology 2015:JCO. 2014.59. 8466.
17. Ishibashi H, Suzuki T, Suzuki S, et al. Progesterone receptor in non-small cell lung cancer—a potent prognostic factor and possible target for endocrine therapy. Cancer Res 2005; 65(14):6450-8.
18. Jonat W, Giurescu M, Robertson J F R. The clinical efficacy of progesterone antagonists in breast cancer. Endocrine Ther Breast Cancer 2002 (8):117-124.
19. Jonat W, Bachelot T, Ruhstaller P et al. Randomized phase 2 study of lonaprisan as second line therapy for progesterone receptor positive breast cancer. Ann Oncol 2013; 24: 2543-2548.
20. Kim J J, Kurita T, and Bulun S E. Progesterone Action in Endometrial Cancer, Endometriosis, Uterine Fibroids, and Breast Cancer. Endocrine Rev 2013; 34: 130-162.
21. Klijn J G M, Setyono-Han B, Foekens J A. Progesterone antagonists and progesterone receptor modulators in the treatment of breast cancer. Steroids 2000; 65: 825-830.
22. Koivisto-Korander R, Leminen A and Heikinheimo O. Mifepristone as treatment of recurrent progesterone receptor-positive uterine leiomyosarcoma. Obstetrics and Gynecology 2007; 109: 512-514.
23. Lanari C, Wargon V, Rojas P and Molinolo A A. Antiprogestins in breast cancer treatment: are we ready? Endocrine-Related Cancer 2012; 19: R35-R50.
24. Lange C A, Gioeli D, Hammes S R, and PC Marker. Integration of Rapid Signaling Events with Steroid Hormone Receptor Action in Breast and Prostate Cancer. Annu Rev Physiol 2007; 69:171-99.
25. Lange C A, Sartorius C A, Abdel-Hafiz H, et al. Progesterone Receptor Action: Translating Studies in Breast Cancer Models to Clinical Insights. Innov Endocrinol Cancer 2008; 7:94-110.
26. Mortel R, Zaino R, and Satyaswaroop P G. Heterogeneity and Progesterone-Receptor Distribution in Endometrial Adenocarcinoma. Cancer 1984; 53:113-116.
27. Mote P and Clarke C. Relative expression of progesterone receptors A and B in premalignant and invasive breast lesions. Breast Cancer Research 2000; 2 (Suppl 1): P2.01 doi:10.1186/bcr103.
28. Mote P A, Bartow S, Tran N, Clarke C L. Loss of co-ordinate expression of progesterone receptors A and B is an early event in breast carcinogenesis. Breast Cancer Res Treat 2002; 72(2):163-72.
29. Mote P A, Graham J D, Clarke C L. Progesterone receptor isoforms in normal and malignant breast. Ernst Schering Found Symp Proc. 2007; (1):77-107.
30. Mueller M D, Vigne J L, Pritts E A et al. Progestins activate vascular endothelial growth factor gene transcription in endometrial adenocarcinoma cells. Fertil Steril 2003; 79: 386-392.
31. Rezai K, Cottu P H, Huguet S et al. Population pharmacokinetic (PPK) modeling of onapristone in patients (pts) with progesterone receptor (PR)-expressing cancers. AACR Annual Meeting 2015. Abstract 4523.
32. Robertson J F R, Willsher P C, Winterbottom L et al. Onapristone, a Progesterone Receptor Antagonist, as First-line Therapy in Primary Breast Cancer. Eur J Cancer 1999; 35: 214-218.
33. Sieh W, Köbel M, Longacre T A, et al. Hormone-receptor expression and ovarian cancer survival: an Ovarian Tumor Tissue Analysis consortium study. Lancet Oncol 2013; http://dx.doi.org/10.1016/S1470-2045(13) 70253-5.
34. Taplin M E, Manola J, Oh W et al. A phase II study of mifepristone (RU-486) in castration-resistant prostate cancer, with a correlative assessment of androgen-related hormones. J Compil B J U Int 2008; 101: 1084-1089.
35. Thigpen J T, Brady M, Alvarez R et al. Oral Medroxyprogesterone Acetate in the Treatment of Advanced or Recurrent Endometrial Carcinoma: A Dose-Response Study by the Gynecologic Oncology Group. J Clin Oncol 1999; 17: 1736-1744.
36. Yin P, Lin Z, Reierstad S, et al. Transcription Factor KLF11 Integrates Progesterone Receptor Signaling and Proliferation in Uterine Leiomyoma Cells. Cancer Res 2010; 70(4); 1722-30.

What is claimed is:

1. An extended release pharmaceutical composition comprising about 5% (wt/wt) onapristone, wherein the onapristone is present in an amount from about 2 mg to about 50 mg, and wherein the $C_{max}$ of onapristone following the administration of the extended release formulation to a patient is at least about 240 ng/ml over about 8-12 hours.

2. The extended release pharmaceutical composition of claim 1, wherein the dosage form of the pharmaceutical composition is selected from the group consisting of tablets and capsules.

3. The extended release pharmaceutical composition of claim 1, wherein the purity of the onapristone is at least about 98%.

4. The extended-release pharmaceutical composition of claim 1, wherein the ratio of onapristone to inactive excipients is about 0.05 to about 5% (wt/wt).

5. The extended release pharmaceutical composition of claim 1, wherein the onapristone is present in an amount selected from the group consisting of about 2 mg, 2.5 mg, 5 mg, 10 mg, 20 mg, 25 mg, 37.5 mg, and 50 mg.

6. The extended release pharmaceutical composition of claim 1, wherein the AUC of onapristone following the administration of 10 mg of the extended release formulation to a patient twice per day is at least about 1578 ng*h/ml over about 8-12 hours.

7. The extended release pharmaceutical composition of claim 1, wherein a steady state plasma concentration is achieved at about 8 days following the administration of the extended release pharmaceutical composition to a patient twice per day.

8. The extended release pharmaceutical composition of claim 1, wherein the composition comprises a cellulose.

9. The extended release pharmaceutical composition of claim 8, wherein the cellulose comprises hydroxypropyl methylcellulose and microcrystalline cellulose.

10. A method of administering onapristone to a patient having cancer comprising administering an extended release onapristone pharmaceutical composition of claim 1 at least once per day to the patient.

11. The method of claim 10, wherein the extended release onapristone pharmaceutical composition is administered twice per day.

12. The method of claim 10, wherein the onapristone it at least about 98% pure.

13. The method of claim 10, wherein the amount of onapristone in the extended release onapristone pharmaceutical composition is selected from the group consisting of about 2 mg, 2.5 mg, 5 mg, 10 mg, 20 mg, 25 mg, 37.5 mg and 50 mg.

14. The method of claim 10, wherein the cancer expresses the progesterone receptor.

15. The method of claim 14, wherein the cancer is selected from the group consisting of breast, prostate, ovarian, and uterine endometrioid cancers.

16. A method of treating a human subject having a disorder capable of treatment with onapristone comprising administering the extended release onapristone pharmaceutical composition of claim 1 to the human subject, wherein the AUC of onapristone following the administration of 10 mg of the extended release formulation to a patient is at least about 1578 ng*h/ml over about 8-12 hours, wherein the disorder is selected from the group consisting of breast cancer, endometrial cancer, prostate cancer, ovarian, uterine endometrioid cancers, and other types of cancer which express the progesterone receptor.

17. The method of claim 16, wherein the extended release onapristone pharmaceutical composition is administered to the human subject once per day or twice per day.

18. A method of treating a human subject having a disorder capable of treatment with onapristone comprising administering to said subject 10 mg of the extended release onapristone pharmaceutical composition of claim 1, wherein the Cmax of onapristone in the human subject is at least about 240 ng/ml over about 8-12 hours, wherein the disorder is selected from the group consisting of breast cancer, endometrial cancer, prostate cancer, ovarian, uterine endometrioid cancers, and other types of cancer which express the progesterone receptor.

19. The method of claim 18, wherein the extended release onapristone pharmaceutical formulation is administered to the human subject once per day or twice per day.

20. A method of treating a human subject having a disorder capable of treatment with onapristone comprising administering to said subject the extended release pharmaceutical composition of claim 1, wherein a steady state plasma concentration is achieved at about 8 days, wherein the disorder is selected from the group consisting of breast cancer, endometrial cancer, prostate cancer, ovarian, uterine endometrioid cancers, and other types of cancer which express the progesterone receptor.

21. The method of claim 20, wherein the extended release onapristone pharmaceutical formulation is administered to the human subject once per day or twice per day.

* * * * *